United States Patent [19]

Bungay

[11] 4,429,272
[45] Jan. 31, 1984

[54] APPARATUS FOR INDICATING DIELECTRIC CONSTANT

[75] Inventor: Michael R. Bungay, Sudbury, England

[73] Assignee: Lucas Industries Limited, Birmingham, England

[21] Appl. No.: 318,433

[22] Filed: Nov. 5, 1981

[30] Foreign Application Priority Data

Feb. 18, 1981 [GB] United Kingdom ............... 8105149

[51] Int. Cl.³ .......................................... G01R 27/26
[52] U.S. Cl. ........................... 324/61 R; 324/60 CD; 324/61 QS
[58] Field of Search ............. 324/61 R, 60 CD, 60 C, 324/61 QS; 73/61 R, 61.1 R, 304 C; 307/265

[56] References Cited

U.S. PATENT DOCUMENTS

| | | | |
|---|---|---|---|
| 3,037,165 | 5/1962 | Kerr | 324/61 R |
| 4,001,676 | 1/1977 | Hile et al. | 324/60 CD |
| 4,065,715 | 12/1977 | Jaffe et al. | 324/60 CD |
| 4,065,721 | 12/1977 | Rabe | 307/265 X |
| 4,228,393 | 10/1980 | Pile | 324/61 QS X |
| 4,240,028 | 12/1980 | Davis, Jr. | 324/61 QS X |

FOREIGN PATENT DOCUMENTS

| | | | |
|---|---|---|---|
| 52-57859 | 5/1977 | Japan | 324/61 R |
| 56-166412 | 12/1981 | Japan | 324/61 R |

Primary Examiner—Stanley T. Krawczewicz

[57] ABSTRACT

An apparatus for providing an indication of a change in the dielectric constant of a fluid comprises a pair of electrodes at least one of which in use is surrounded by the fluid, an oscillator operable to charge and discharge the capacitors formed by the electrodes, the frequency of oscillation of the oscillator being dependent upon the voltage developed across one of the capacitors, and means responsive to the difference in the voltages developed across the capacitors.

9 Claims, 4 Drawing Figures

APPARATUS FOR INDICATING DIELECTRIC CONSTANT

This invention relates to an apparatus for providing an indication of a change in the dielectric constant of a base fluid and more particularly to an apparatus for providing an indication of the presence of a contaminant in the base fluid.

The object of the invention is to provide an apparatus of the kind specified in a simple and convenient form.

According to the invention an apparatus for providing an indication of a change in the dielectric constant of a fluid comprises a pair of electrodes at least one of which is surrounded in use by said fluid, an oscillator operable to charge and discharge capacitors formed by said electrodes respectively, the frequency of oscillation of said oscillator being dependent upon the voltage developed across either one of said capacitors during a cycle and means responsive to the difference in the voltages developed across said capacitors, said means providing an indication of a change in the dielectric constant of the fluid.

In the accompanying drawings

Figure 1:
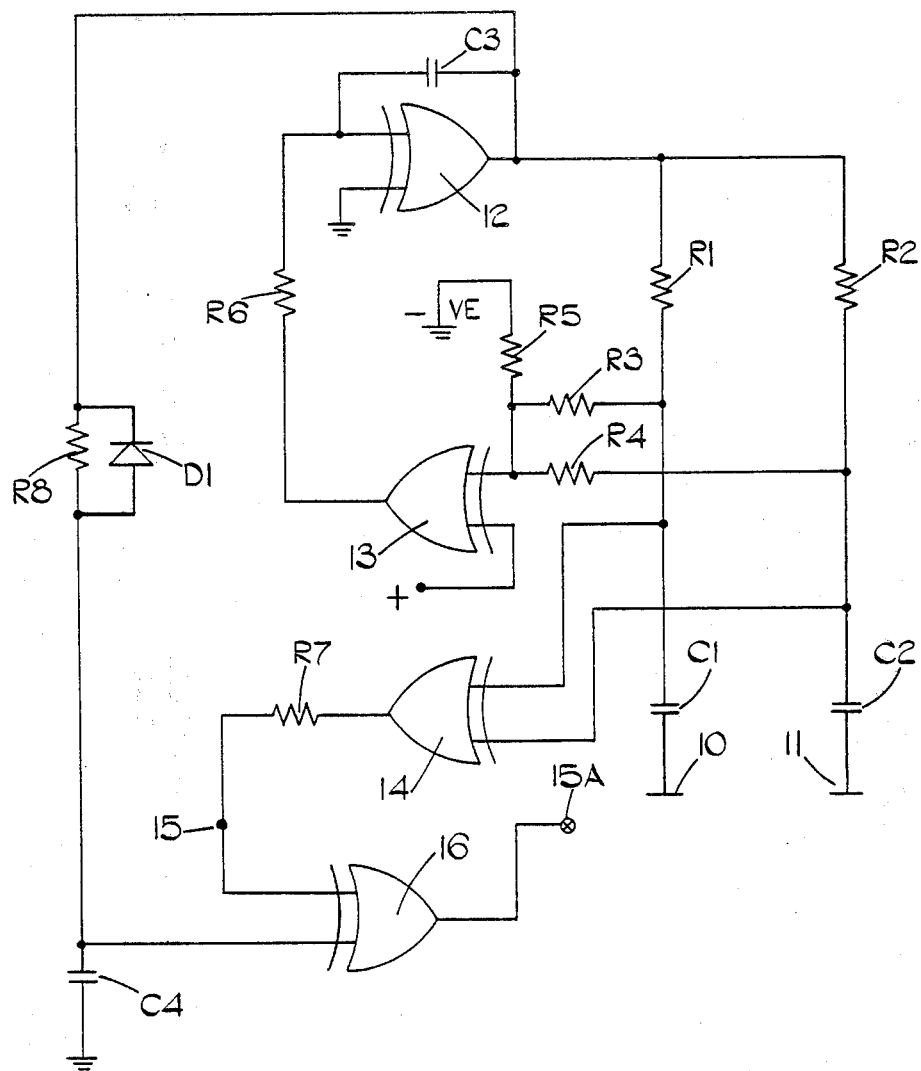
Figure 2:
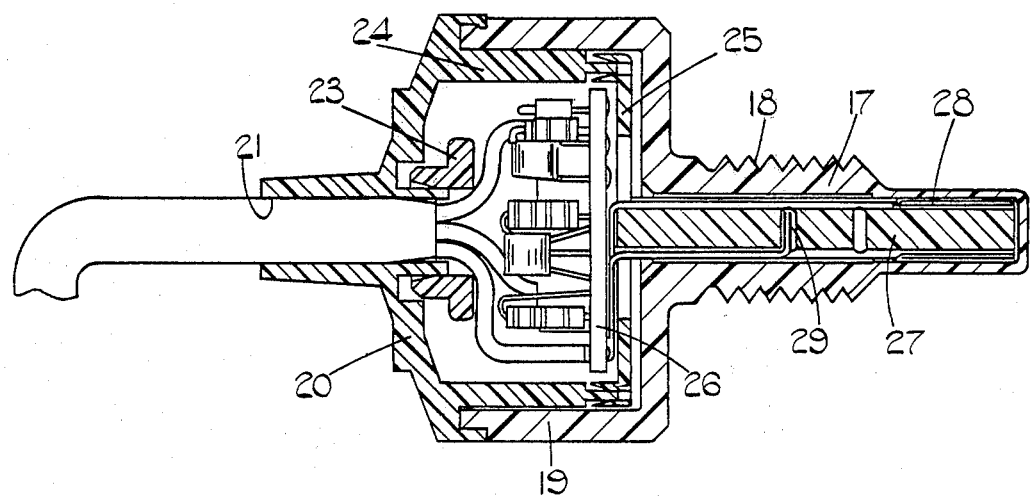
Figure 3:
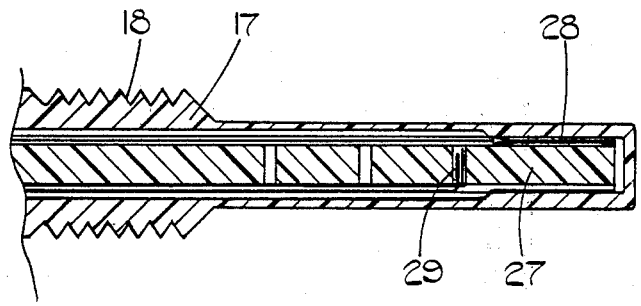
Figure 4:
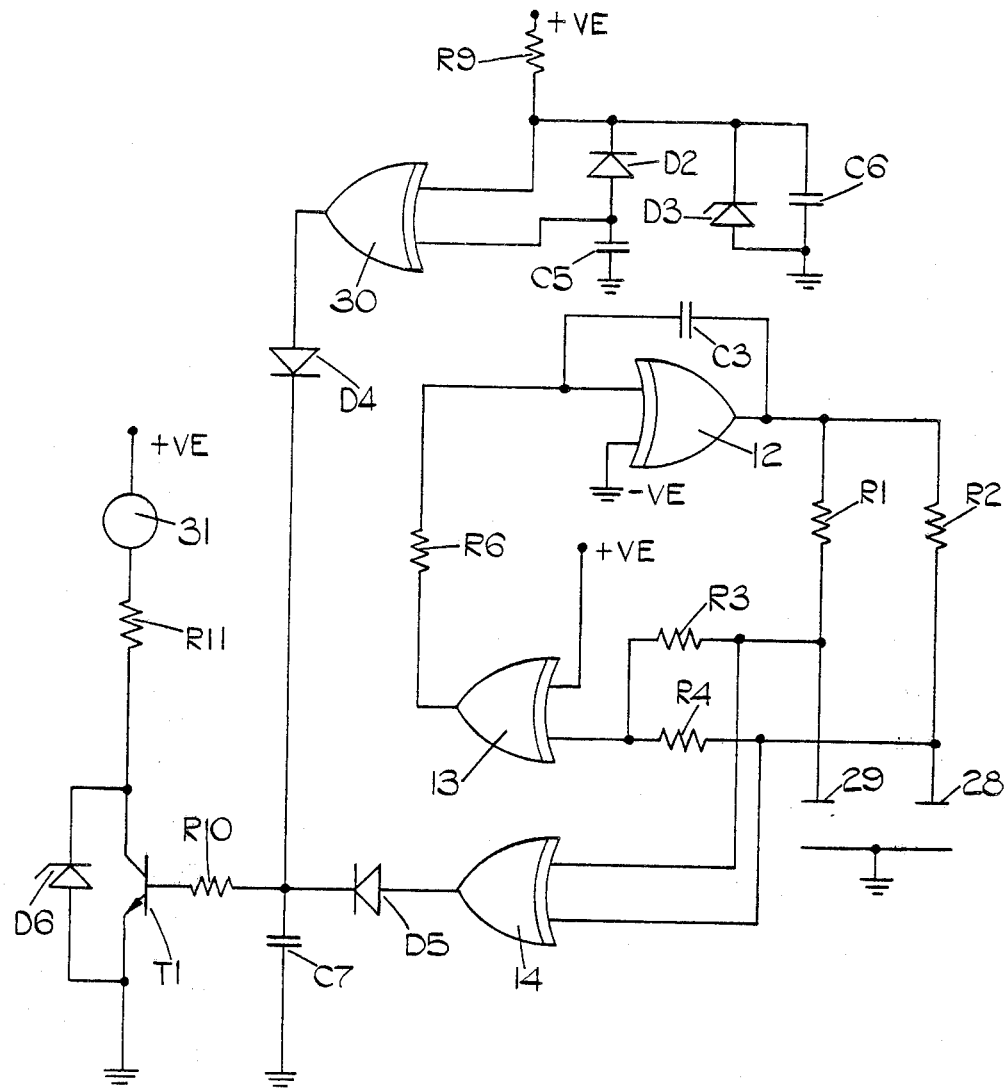

FIG. 1 is a circuit diagram of an example of an apparatus for providing an indication of a rising water level in a sedimentation chamber of an engine fuel system, FIG. 2 is a sectional side elevation of one example of an apparatus for the same purpose, FIG. 3 shows a modification to the apparatus of FIG. 2, and FIG. 4 shows a circuit diagram of the apparatus shown in FIG. 2.

In an engine fuel system it is the usual practice to provide a fuel filter which can remove solid contaminent from the liquid fuel, and a sedimentation chamber in the base of which in use, water contained in the fuel tends to accumulate. It is necessary to drain this water from the chamber when it reaches a certain level otherwise the water can be drawn or forced into the downstream fuel system and in particular the carburettor or fuel injection system. Unfortunately a batch of fuel may contain a substantial amount of water so that draining of the water at regular times or milage intervals may not be sufficient to ensure that water does not pass into the downstream fuel system. It is therefore desirable that some indication should be given to the engine operator that the water level is approaching the aforesaid certain level.

With reference to FIG. 1, the apparatus comprises a pair of electrodes 10, 11 which are mounted upon a support member which is arranged to extend into the sedimentation chamber. Each electrode is connected to one plate of a respective capacitor C1, C2 the other plates of which are connected by way of resistors R1, R2 respectively to the output of a first exclusive OR circuit 12. In addition the aforesaid plates of the capacitors are connected by way of resistors R3, R4 respectively to an input terminal of a second exclusive OR circuit 13 which is also connected to a negative supply terminal by way of a resistor R5. The other input of the circuit 13 is connected to a positive supply terminal and its output by way of a resistor R6 to one input of the circuit 12 the other input of which is connected to the negative supply terminal. A capacitor C3 is connected between the output and the one input of the circuit 12.

The portion of the apparatus thus far described operates as an oscillator the operation of which is as follows. Starting from the instant at which the output of circuit 12 goes high, when this occurs the combined capacitors formed by capacitor C1 and the electrode 10 and by capacitor C2 and the electrode 11 are charged by way of resistors R1 and R2 respectively. The voltages developed across the combined capacitors are applied to the circuit 13 by way of resistors R3 and R4 and when a so called threshold value is reached as determined by the ratios of resistors R3/R4 to R5 the output of circuit 13 goes low causing the output of circuit 12 to go low. In this situation the combined capacitors discharge quickly and the output of circuit 13 will again go high. Circuit 12 will not however switch immediately so that its output becomes high, because of the delaying effect of resistor R6 and capacitor C3. This is to allow time for the combined capacitors to discharge. However, when the circuit does switch capacitor C3 provides positive feedback to speed up the switching operation. The cycle as described is then repeated. The overall frequency of operation is controlled by the combined capacitor which exhibits the lower capacitance value since the voltage across this will rise more quickly. The values of capacitors C1 and C2 are fixed and are higher than the capacitance values of the electrodes so that it is the capacitance values of the electrodes which in practice determine the frequency of operation. The dielectric constant of the fuel can vary for a number of reasons and hence the frequency of oscillation will vary as the fuel dielectric constant varies.

The voltages developed across the combined capacitors are applied to the inputs of a third exclusive OR circuit 14 the output of which can be connected by way of resistor R7 to an output terminal 15. The circuit 14 will have a low output so long as the voltage across the combined capacitors remain substantially the same during the charging period. If however one of the voltages rises more quickly than the other then the output of circuit 14 will become high and will remain high until the other voltage attains the threshold voltage at which instant the output will go low or in the case where the other voltage never reaches the threshold voltage, when the one voltage falls below the threshold value after the output of circuit 12 has become low. If the fuel surrounding one of the electrodes is contaminated with water then its dielectric constant will be different and this is reflected in the pulse width at the output terminal 15. If the type of fuel varies then the dielectric constant of the fuel varies and the frequency of oscillation will vary since this depends upon the minimum electrode capacity which will in most case be due to the uncontaminated fuel. It is therefore possible to provide an indication of water contamination of the fuel even though the type of fuel may change.

It is possible for both electrodes to be surrounded by fuel which is contaminated with water in this case the situation at gate 14 would be the same as is the case where both electrodes are surrounded by uncontaminated fuel. In order to take account of this situation a fourth exclusive OR circuit 16 is provided which has its output connected to an output terminal 15A. One input of the circuit 16 is connected to the terminal 15 and the other input is connected to one plate of a capacitor C4 the other plate of which is connected to the negative supply terminal. The other input of the circuit 16 is also connected by way of resistor R8, to the output of circuit 12, the resistor being bridged by a diode D1 having its cathode connected to the output circuit 12 when the output of circuit 12 goes high capacitor C4 is charged by way of resistor R8 and the values of resistor R8 and capacitor C4 are such that normally i.e. when one or both of the electrodes is surrounded by uncontaminated fuel, the voltage across the capacitor does not reach the threshold voltage of circuit 16 before the output of circuit 12 goes low. In other words circuit 16 does not operate. If both electrodes are surrounded by contaminated fuel then there is time for capacitor C4 to charge so that the output of circuit 16 becomes high before the output of circuit 12 becomes low. The diode D1 acts to discharge capacitor C4 rapidly when the output of circuit 12 becomes low.

The output terminals 15 or 15A can be connected to an indicating device and if the circuit elements are suitably chosen it is possible to obtain an indication of the dielectric constant of the fuel surrounding the electrodes. The signals at the output terminals 15 or 15A can be integrated and used to operate a warning lamp to provide a visual warning that the fuel is contaminated with water to an excessive degree.

In another arrangement practical embodiments of which are seen in FIGS. 2 and 3, the electrodes are encapsulated to prevent direct contact with the fuel. Moreover, the electrical circuit is modified as will be explained. With reference to FIG. 2 the apparatus comprises a tubular casing 17 which is closed at its narrower end and which is provided with a peripheral screwthread 18 whereby it can be mounted within a threaded aperture in the base wall of the sedimentation chamber. The casing has an enlarged portion 19 the open end of which is closed by a closure member 20 which defines a cable aperture 21 through which extends the connecting cable 22. A cable retainer 23 is provided which when pressed into position deforms a portion of the closure member about the cable to form a fluid tight seal.

The closure member has an integral skirt portion 24 which extends within the enlarged portion 19 of the casing. The skirt portion provides location for an annular support member 25 which besides providing a mounting for a circuit board 26 also carries a cylindrical mounting member 27 which extends within the narrower portion of the casing. The mounting member 27 is formed from electrically insulating materials as also is the casing. The end portion of the mounting member is surrounded by an electrode 28 which may be for example, a foil. The electrode 28 is connected to the circuit board by an insulated wire. A second electrode 29 is inserted in a transverse bore in the mounting member and is also connected to the circuit board by means of an insulated wire. In this case it will be noted that the electrode 28 is larger in area than the electrode 29 and that both electrodes are encapsulated and do not contact the fuel. As will be seen from the modified circuit diagram the fact that the electrodes are encapsulated makes it possible to eliminate the fixed capacitors which were connected in series with the electrodes of FIG. 1. When the casing 17 is secured in the sedimentation chamber the electrode 29 is in effect surrounded by the material forming the chamber. Its capacitance value will therefore be substantially constant irrespective of changes in the fuel.

FIG. 3 of the drawings shows a modification of the practical embodiment. In FIG. 3 the casing and also the mounting member are much longer so that the electrode 29 is well clear of the threaded portion 18 of the casing and is also well clear of the base wall of the sedimentation chamber. As shown in both FIG. 2 and 3 alternative bores can be provided for the electrode 29.

Turning now to FIG. 4, it will be seen that besides the capacitors C1 and C2 the resistors R5, R6, R7 and R8 are omitted together with capacitors C3 and C4, diode D1 and exclusive OR circuit 16.

The circuit of FIG. 4 includes an exclusive OR circuit 30 having one input connected to a positive supply terminal by way of a resistor R9 and its other input connected to a negative supply terminal by way of a capacitor C5. The inputs are interconnected by a diode D2 and the one input is connected to the negative supply terminal by way of a capacitor C6 which is bridged by a zener diode D3. It will be noted that the cathode of diode D2 is connected to the aforesaid one input.

The output terminal of circuit 30 is connected to the anode of a diode D4 the cathode of which is connected to one end of a resistor R10 and to one plate of a capacitor C7. The other plate of the capacitor is connected to the negative supply terminal. Moreover, also connected to the one end of the resistor R10 is the cathode of a diode D5 the anode of which is connected to the output terminal of the circuit 14.

The other end of the resistor R10 is connected to the base terminal of a transistor T1 the emitter terminal of which is connected to the negative supply terminal and the collector of which is connected to one end of a resistor R11 the other end of which is connected by way of a warning lamp 31 to the positive supply terminal. A zener diode D6 is connected between the collector and emitter terminals of the transistor.

The operation of the circuits 12 and 13 together with the associated components is substantially the same as described with reference to FIG. 1. In this case however resistor R5 is omitted.

The circuit 14 as with the example of FIG. 1, is responsive to the difference between the voltages developed across the capacitors constituted by the electrodes 28, 29. Even though one electrode is larger than the other, when the fuel is uncontaminated the difference in the capacities is very small and although the output of circuit 14 may go high it will do so for a short time only and because of the capacitor C7 the transistor T1 will not be turned on. If however the fuel is contaminated, the difference in the capacities of the electrodes will be larger and the output of the circuit 14 will remain high for a longer period of time so that the transistor will be turned on to cause illumination of the warning lamp.

The circuit 30 together with the associated components serves as a timer for the purpose of testing the warning lamp each time the circuit is connected to a source of electric supply. Before such connection is made the capacitors C5 and C6 will be in a discharged state. When the connection is made capacitor C6 will charge to a voltage determined by the zener diode D3 fairly quickly. However capacitor C5 is charged by the reverse leakage current of the diode D2 and hence charges to the voltage determined by the zener diode much more slowly. During the period of inequality of the voltages at the inputs of the circuit 30 its output is high with the result that the transistor is turned on and the lamp illuminated.

I claim:
1. Apparatus for providing an indication of a change in the dielectric constant of a fluid comprising a pair of electrodes, at least one of which in use is surrounded by said fluid, an oscillator operable to charge and dis- charge capacitors formed by said electrodes, said oscillator including a pair of exclusive OR circuits, a first pair of resistors connecting the output of one of said exclusive OR circuits to said capacitors respectively, a second pair of resistors connecting the capacitors respectively to one input of the other exclusive OR circuit, the output of said other exclusive OR circuit being connected in use to one input of said one exclusive OR circuit, the other inputs of the exclusive OR circuits being connected to opposite polarity supply lines respectively, the frequency of oscillation of said oscillator being dependent upon the rate of change of voltage across either one of said capacitors during a cycle, and means responsive to the difference in the voltages developed across said capacitors, said means providing an indication of a change in the dielectric constant of the fluid.

2. An apparatus according to claim 1 including a resistor connected between the output of said other circuit and the one input of the one circuit, and a capacitor connected between the one input of the one circuit and its output.

3. An apparatus according to any one of claims 1 or 2 including a further exclusive OR having its inputs connected to said capacitors respectively and its output connected to an indicating circuit.

4. An apparatus according to claim 3 in which said indicating circuit includes a transistor the collector/emitter path of which is connected in series with a warning lamp, the output of said further exclusive OR circuit being connected to the base of said transistor by way of a resistor.

5. An apparatus according to claim 4 including a capacitor operable to delay the conduction of the transistor following a change in the output of the further exclusive OR circuit.

6. An apparatus according to claim 5 including an additional exclusive "OR" circuit connected as a timer to provide base current to said transistor for a limited period of time for the purpose of testing said warning lamp when the apparatus is connected to a source of supply.

7. An apparatus according to claim 1 in which said capacitors are formed by the electrodes and fixed capacitors connected in series therewith, said electrodes being carried upon an insulated support for immersion in the fluid.

8. An apparatus according to claim 1 in which said electrodes are mounted within an insulating support arranged to be immersed in the fluid.

9. An apparatus according to claim 1 in which the areas of the two electrodes are different.

* * * * *